(12) United States Patent
Mihashi

(10) Patent No.: US 11,109,754 B2
(45) Date of Patent: Sep. 7, 2021

(54) OPHTHALMIC MEASUREMENT DEVICE

(71) Applicant: TOPCON CORPORATION, Tokyo (JP)

(72) Inventor: Toshifumi Mihashi, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 201 days.

(21) Appl. No.: 16/478,191

(22) PCT Filed: Jan. 24, 2018

(86) PCT No.: PCT/JP2018/002102
§ 371 (c)(1),
(2) Date: Jul. 16, 2019

(87) PCT Pub. No.: WO2018/139481
PCT Pub. Date: Aug. 2, 2018

(65) Prior Publication Data
US 2019/0365222 A1 Dec. 5, 2019

(30) Foreign Application Priority Data
Jan. 25, 2017 (JP) .............................. JP2017-011131

(51) Int. Cl.
*A61B 3/103* (2006.01)
*A61B 3/00* (2006.01)
*A61B 3/14* (2006.01)

(52) U.S. Cl.
CPC ............ *A61B 3/103* (2013.01); *A61B 3/0025* (2013.01); *A61B 3/14* (2013.01)

(58) Field of Classification Search
CPC ......... A61B 3/103; A61B 3/0025; A61B 3/14; A61B 3/0008
(Continued)

(56) References Cited

U.S. PATENT DOCUMENTS 7,311,402 B2 * 12/2007 Mihashi .............. A61B 3/1015
351/205
2006/0126018 A1 6/2006 Liang
(Continued)

FOREIGN PATENT DOCUMENTS

JP 2007330585 A 12/2007
JP 4392006 B2 12/2009
(Continued)

OTHER PUBLICATIONS

International Search Report and Written Opinion dated Apr. 17, 2018 in connection with International Patent Application No. PCT/JP2018/002102, 10 pgs.

*Primary Examiner* — Mohammed A Hasan
(74) *Attorney, Agent, or Firm* — Chiesa Shahinian & Giantomasi PC

(57) ABSTRACT

Provided is an ophthalmic measurement device with which it is possible to obtain an area in which a measurement can be taken without moving an optical system. With reference to an optical path length of an illumination optical system with which light is focused on the eyeground when the refraction value is 0 D, the positions of two light sources are set to achieve a setting in which the optical path length becomes slightly shorter. By doing so, it is possible to cope with measurement of refractive properties in a large area without employing structures that allow a lens system of the illumination optical system and the light sources thereof to be moved. In addition, by selecting one of the two light sources so that a clearer Hartmann image can be obtained, it is possible to further increase the precision of the refractive properties to be measured.

10 Claims, 3 Drawing Sheets

(58) Field of Classification Search
USPC .......................................................... 351/206
See application file for complete search history.

(56) References Cited

U.S. PATENT DOCUMENTS

| | | | |
|---|---|---|---|
| 2007/0291229 A1 | 12/2007 | Yamaguchi et al. | |
| 2015/0009357 A1 | 1/2015 | Seibel et al. | |
| 2015/0057701 A1* | 2/2015 | Kelleher | A61B 90/30 606/204.15 |

FOREIGN PATENT DOCUMENTS

| | | |
|---|---|---|
| JP | 2014030573 A | 2/2014 |
| JP | 2015508685 A | 3/2015 |
| WO | 2007064362 A1 | 6/2007 |
| WO | 2013123461 A1 | 8/2013 |

* cited by examiner

OPHTHALMIC MEASUREMENT DEVICE

CROSS-REFERENCE TO RELATED APPLICATIONS

This application is a National Stage under 35 U.S.C. 371 of PCT/JP2018/002102, filed Jan. 24, 2018, which is based upon and claims benefit of priority from Japanese Patent Application No. 2017-011131, filed Jan. 25, 2017, the entire contents of which are incorporated herein by reference.

TECHNICAL FIELD

The present invention relates to an ophthalmic measurement device characterized by having an illuminating optical system.

BACKGROUND ART

An ophthalmic measurement device for measuring information relating to refraction characteristics of a subject's eye is publicly known. This ophthalmic measurement device measures a refracted wavefront of reflected light that is reflected back from the subject's eye. The ophthalmic measurement device may have a structure for adjusting an illuminating optical system and a light receiving optical system independently of each other. An example is disclosed in Patent Literature 1.

CITATION LIST

Patent Literature

Patent Literature 1: Japanese Patent No. 4392006

SUMMARY OF INVENTION

Technical Problem

A mechanism for adjusting an optical system requires a structure to cause, for example, lenses in the optical system, to move. To make the optical system move, structural dimensions for securing space for the movement and a driving mechanism for the movement are necessary. These requirements interfere with reduction in size and reduction in weight of the device, simplification of the structure, reduction in cost, ensuring high reliability, and reduction in consumption of electric power. In view of these circumstances, an object of the present invention is to provide an ophthalmic measurement device that enables securing a measurable range without having the optical system move.

Solution to Problem

A first aspect of the present invention provides an ophthalmic measurement device including an illuminating optical system, a light receiving optical system, and a computing unit. The illuminating optical system has an illumination light source that illuminates an eyeground of a subject's eye. The light receiving optical system has a Hartman plate and a light receiving unit. The Hartman plate is configured to split the flux of reflected light that is reflected back from the eyeground of the subject's eye into multiple light fluxes. The light receiving unit is configured to receive light fluxes that are obtained as a result of splitting by the Hartman plate. The computing unit calculates optical characteristics of the subject's eye from data of a tilt angle of the light flux obtained by the light receiving optical system. The illumination light source is disposed at a predetermined position. A structure for moving light focusing positions of the illuminating optical system and the light receiving optical system is not provided.

A second aspect of the present invention provides an ophthalmic measurement device including an illuminating optical system, a light receiving optical system, and a computing unit. The illuminating optical system has an illumination light source that illuminates an eyeground of a subject's eye. The light receiving optical system has a Hartman plate and a light receiving unit. The Hartman plate is configured to split flux of reflected light that is reflected back from the eyeground of the subject's eye into multiple light fluxes. The light receiving unit is configured to receive light fluxes that are obtained as a result of splitting by the Hartman plate. The computing unit calculates optical characteristics of the subject's eye from data of a tilt angle of the light flux obtained by the light receiving optical system. The illumination light source is disposed at a predetermined position so that a predetermined range of measurable refraction value is secured without having to move light focusing positions of the illuminating optical system and the light receiving optical system.

According to a third aspect of the present invention, in the first or the second aspect of the present invention, an optical path length of the illuminating optical system may be fixed, and the predetermined position of the illumination light source may be set so that the optical path length is shorter than the optical path length in a case of focusing light on the eyeground in measuring the subject's eye with 0 D.

According to a fourth aspect of the present invention, in the third aspect of the present invention, the optical path length may be set in a range that is approximately 2.5 to 3 mm shorter than the optical path length in measuring the subject's eye with 0 D.

According to a fifth aspect of the present invention, in any one of the first to the fourth aspects of the present invention, the computing unit may perform image processing on an image obtained by the light receiving optical system and obtain the data of the tilt angle from the image that is subjected to the image processing.

According to a sixth aspect of the present invention, in any one of the first to the fifth aspects of the present invention, the illuminating optical system may have multiple illumination light sources that are disposed so as to have different light focusing positions.

According to a seventh aspect of the present invention, in any one of the first to the sixth aspects of the present invention, the illuminating optical system may have multiple optical paths of different lengths.

Advantageous Effects of Invention

The present invention provides an ophthalmic measurement device that enables securing a measurable range without movement in an optical system.

REFERENCE SIGNS LIST

The reference symbol 100 denotes an ophthalmic measurement device, 102 denotes a lens system, 104 denotes a polarizing beam splitter, 105 denotes an optical diaphragm, 106 denotes a lens system, 107 denotes a dichroic mirror, 108 denotes an objective lens, 109 denotes a dichroic mirror, 112 denotes a light source, 113 denotes a lens system, 114 denotes a light receiving unit, 115 denotes an image-data outputting unit, 116 denotes a computing unit, 150 denotes a subject's eye, 120 denotes a lens system, 121 denotes a Hartman plate, 122 denotes a light receiving unit, 200 denotes an illuminating optical system, 211 denotes an optical component having bundled multiple optical fibers with different lengths, 212 denotes a MEMS optical switch, 213 denotes an optical fiber, and 214 denotes an optical fiber.

DESCRIPTION OF EMBODIMENTS

1. First Embodiment

Figure 1:
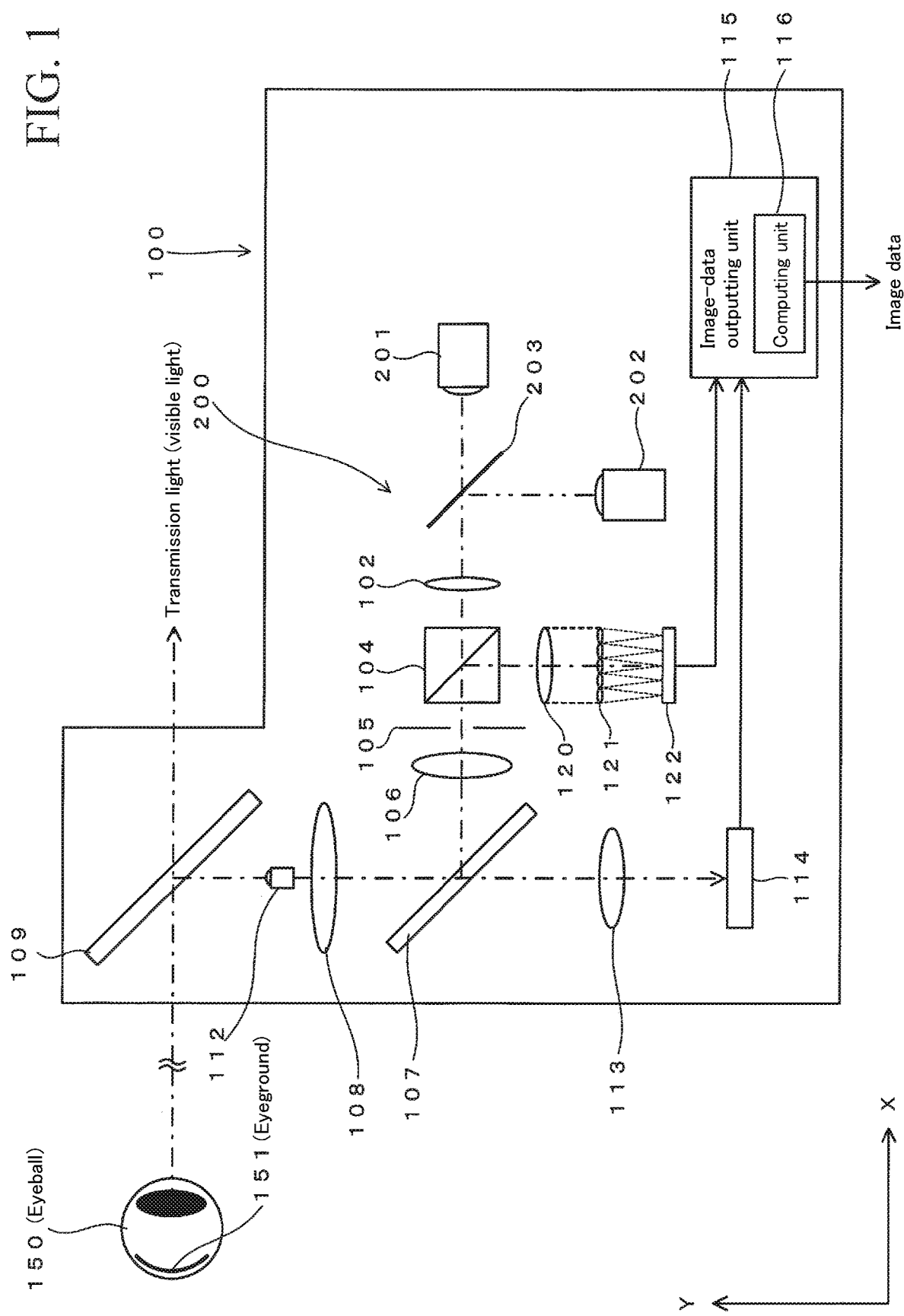
FIG. 1 is a conceptual diagram of an ophthalmic measurement device of an embodiment.

FIG. 1 shows a conceptual diagram of an embodiment using the invention. FIG. 1 shows an ophthalmic measurement device 100 of an embodiment. The ophthalmic measurement device 100 has a function of obtaining information of a refracted wavefront aberration contained in reflected light that is reflected back from an eyeball.

Illuminating Optical System

The ophthalmic measurement device 100 includes an illuminating optical system 200 that emits illumination light to an eyeground 151 of a subject's eye 150. The illuminating optical system 200 includes light sources 201 and 202, a half mirror 203, a lens system 102, a polarizing beam splitter 104, an optical diaphragm 105, a dichroic mirror 107, an objective lens 108, and a dichroic mirror 109.

The light sources 201 and 202 output illumination light to be emitted to the eyeground 151. The light sources 201 and 202 are laser diodes that generate infrared light of a wavelength of 830 nm. The half mirror 203 transmits the light from the light source 201 to the objective lens 102 and reflects the light from the light source 202 to the lens system 102. The distance between the light source 201 and the half mirror 203 is made shorter than the distance between the light source 202 and the half mirror 203. Thus, an optical path length of the illuminating optical system 200 in a case of selecting the light source 201 differs from that in a case of selecting the light source 202. Either one of the light sources 201 and 202 emits light while the other ceases emitting light. Light emissions of these light sources 201 and 202 are switched to select the optical path length as described above. The switching of the light emissions can be performed by use of optical shutters.

The lens system 102 adjusts flux of the light from the light source 201 or 202. The lens system 102 is illustrated in a simplified manner, but the lens system 102 includes multiple lenses in combination in actual use. This also applies to other lens systems described below.

The illumination light from the light source 201 or 202 enters the dichroic mirror 107 via the lens system 102, the polarizing beam splitter 104, the optical diaphragm 105, and the lens system 106. The dichroic mirror 107 reflects this incident light to the upper direction in FIG. 1. The dichroic mirror 107 is configured to reflect light with a wavelength of 830 nm from the light source 201 or 202 and to transmit light with a wavelength of 940 nm. The illumination light that is reflected to the upper direction in FIG. 1 by the dichroic mirror 107 enters the dichroic mirror 109 via the objective lens 108. The illumination light that enters the dichroic mirror 109 is reflected to the left direction in FIG. 1 to the subject's eye 150. The dichroic mirror 109 is structured to open to a direction of line of sight of the subject being examined. The dichroic mirror 109 is configured to transmit visible light in a wavelength range shorter than a wavelength of approximately 800 nm and to reflect infrared light with a wavelength exceeding 800 nm. The illumination light that is reflected to the left direction in the drawing by the dichroic mirror 109 is emitted to the eyeground 151 of the subject's eye 150. The above is a configuration of the illuminating optical system 200.

The illuminating optical system 200 is made to have an optical path length that is slightly shorter relative to an optical path length in a case of focusing the illumination light on the eyeground 151 when measuring a subject's eye of 0 D. As described above, the distance between the light source 201 and the half mirror 203 and the distance between the light source 202 and the half mirror 203 are made different from each other. This enables selecting either one of the set two kinds of the optical path lengths. Details of setting the optical path lengths will be described below.

Figure 2A:
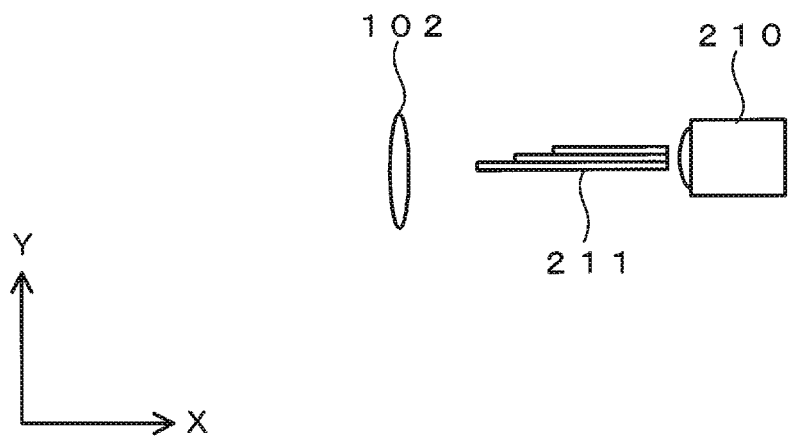
FIGS. 2A and 2B are conceptual diagrams showing examples of an illuminating optical system.
Figure 2B:
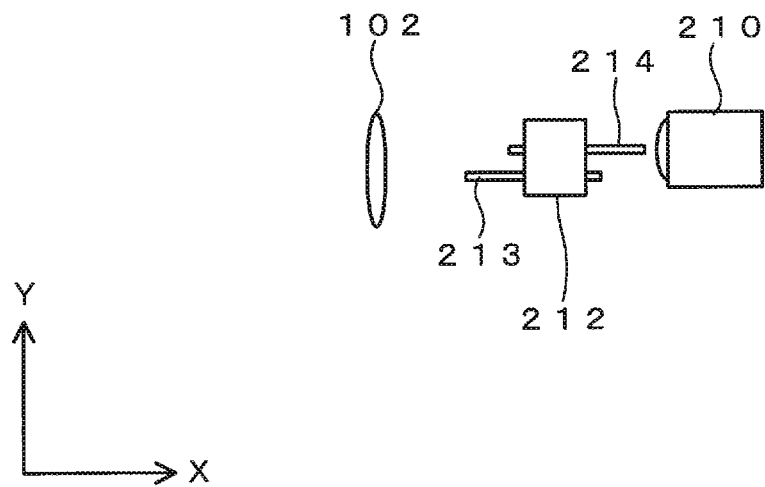

FIGS. 2A and 2B are conceptual diagrams of other examples in the case of setting multiple optical path lengths in the illuminating optical system 200. In the example shown in FIG. 2A, light from the light source 210 is made to enter an optical component 211 having bundled multiple optical fibers of different lengths, whereby light that is emitted from each of the optical fibers of different lengths is made to enter the lens system 102 at the same time. This structure provides multiple kinds of optical path lengths depending on the different lengths of the optical fibers. In this case, three kinds of the optical path lengths are provided. This provides Hartman images including a focused image with a relatively high luminance and a blurred image with a relatively low luminance at the same time. One with a high luminance is detected from among these images by image processing in the condition in which an appropriate threshold is set. This structure is set so that the optical path length of the path of each of the optical fibers will fall within a range, which will be described below. The number of the bundled optical fibers is not limited to three and may be two or four.

FIG. 2B describes a structure that enables selecting either one of a first optical path and a second optical path by means of a MEMS optical switch 212. The first optical path makes light from the light source 210 enter from the optical fiber 214 directly into the lens system 102. The second optical path makes light of the light source 210 enter from the optical fiber 213 to the lens system 102 via the optical fiber 214 and the subsequent optical fiber 213. In this case, effects similar to those in the case of changing the position of a light source are obtained by switching the positions of the light emitted from the optical fibers. In this case, also, the structure is set so that the optical path lengths of the paths to be switched will fall within the range, which will be described later.

Setting of Optical Path Length

Figure 3:
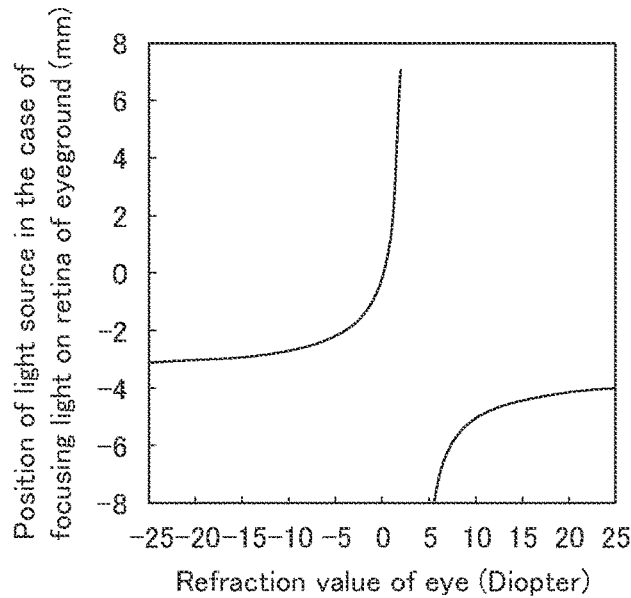
FIG. 3 is a graph showing a relationship between a refraction value (lateral axis) and a position (vertical axis) of a light source of an illuminating system in the condition in which light focuses on a retina of an eyeground.

The following describes a means for obtaining a refraction value in a range as wide as possible in the condition in which the position of a focus of the illuminating optical system is fixed. The refraction value is a parameter for evaluating the degree of tropistic abnormality of an eye. FIG. 3 shows a calculated value (vertical axis) of the position of a light source of an illuminating system in the condition of focusing light on a retina of an eyeground, relative to each refraction value (lateral axis). The light source corresponds to the light source 201 or 202 in FIG. 1. The value of the vertical axis is based on the position of 0 mm that is the position of the light source in the case of focusing illumination light on a retina of an eyeground of a model eye with a refraction value of 0 D. The value of the vertical axis is shown with a minus sign for the position of the light source coming close to the subject's eye, that is, the position of the light source that makes the optical path of the illumination light shorter. The value of the vertical axis is shown with a plus sign for the position of the light source coming away from the subject's eye, that is, the position of the light source that makes the optical path of the illumination light longer. As shown in FIG. 3, for example, the position of the light source in the condition of focusing the illumination light on the eyeground of a measured subject's eye with a refraction value of −15 D is approximately minus 3 mm from the position of the light source in the condition of focusing the illumination light on the eyeground of a measured subject's eye with a refraction value of 0 D.

The graph shown in FIG. 3 has a shape like a hyperbolic curve and diverges at around +3.5 D while +∞ D and −∞ D converge at around −3.5 mm. FIG. 3 suggests that, when the light source is positioned to form an optical path shorter than in the case of being positioned for 0 D, the range in which light focuses is large, and thus, a wider range of the refraction value can be used. That is, it is suggested that a wide range of the refraction value can be measured by slightly shortening the optical path length in the condition in which the illumination light focuses on an eyeground, from the optical path length for 0 D.

On the basis of this knowledge, the following preliminarily experiment was performed. First, the position of the light source, at which light focuses on an eyeground, was obtained in measuring each of the refraction values of +15 D, +10 D, 0 D, −10 D, and −15 D. Thereafter, in these obtained conditions, nine model eyes with approximately no aberration and having positions as shown in Table 1 were measured.

In more detail, the measurement was performed as follows. For example, a Hartman image at the position of the model eye shown in Table 1 was observed in the condition in which the illumination light focuses on a retina of an eyeground in measurement of the refraction value of +15 D. Similarly, a Hartman image at the position of the model eye shown in Table 1 was observed in the condition in which the illumination light focuses on the retina of the eyeground in measurement of the refraction value of +10 D. The Hartman image that was obtained in each condition was processed by image analysis software, whereby a refraction value was calculated. The case of successfully calculating the refraction value from the Hartman image by means of the image analysis software is indicated by a mark "○", whereas the case of failing to calculate the refraction value is indicated by a mark "x", and thus, these results are sorted. These results are shown in Table 2.

TABLE 2

| Light focusing position | Deviated amount from position for 0D (mm) | Position of model eye | | | | | | | | |
|---|---|---|---|---|---|---|---|---|---|---|
| | | −24.68 (−24D) | −15.76 (−15D) | −10.55 (−10D) | −5.91 (−5D) | −0.95 (−0D) | 4.22 (+5D) | 9.51 (+10D) | 14.51 (+15D) | 21.87 (+22D) |
| −15D | −2.93 | ○ | ○ | ○ | ○ | ○ | ○ | ○ | ○ | ○ |
| −10D | −2.70 | ○ | ○ | ○ | ○ | ○ | ○ | ○ | ○ | ○ |
| 0D | 0.00 | x | x | ○ | ○ | ○ | ○ | x | x | x |
| +10D | −5.00 | x | x | ○ | ○ | ○ | ○ | ○ | ○ | x |
| +15D | −4.38 | x | x | ○ | ○ | ○ | ○ | ○ | ○ | x |

Table 2 shows a "light focusing position" that represents a refraction value in the condition in which the focused position of the illumination light is adjusted so as to be on the retina of the eyeground. The "deviated amount from the position for 0 D" represents that an amount of deviation from the position of the light source in the condition in which the focused position of the illumination light is adjusted so as to be on the retina of the eyeground of the model eye with 0 D. The deviated amount has a minus sign when the light source deviates toward the subject's eye to cause the optical path length to be shorter, whereas the deviated amount has a plus sign when the light source deviates away from the subject's eye to cause the optical path length to be longer.

As is clearly shown in Table 2, a wider range of the refraction value, ranging from −25 to +22, can be measured by shortening the optical path length by a little less than 3 mm from the optical path length of the illuminating optical system in the condition in which light focuses on an eyeground with a refraction value of 0 D.

In consideration of the results in Table 2 together with the data in FIG. 3, it is concluded that a wider range of the refraction value can be measured in the condition of fixing the optical path length of the illuminating optical system by setting the optical path length in a range that is approximately 2.5 to 3 mm shorter than the optical path length of the illuminating optical system in which light focuses on an eyeground with a refraction value of 0 D. This condition is

TABLE 1

| Approximation name | −24D | −15D | −10D | 0D | +5D | +10D | +15D | +22D |
|---|---|---|---|---|---|---|---|---|
| Position of model eye | −24.68 | −15.76 | −10.55 | −5.91 | 4.22 | 9.51 | 14.51 | 21.87 | referred as a "first condition". On the other hand, the measurable range of the refraction value can also be widened by setting the optical path length so as to be approximately 4 to 5 mm longer than the optical path length of the illuminating optical system in which light focuses on an eyeground with a refraction value of 0 D. This condition is referred as a "second condition". However, compared with the case of the first condition, the measurable range is narrow in the second condition. In particular, in the second condition, the refraction values of −15 and −24 D cannot be measured, and the refraction value of +22 D also cannot be measured.

Calibration of Data

As shown in Table 2, a wider range of the refraction value can be measured in the condition of fixing the optical path length of the illuminating optical system, by slightly shortening the optical path length of the illuminating optical system from the optical path length of the illuminating optical system in which light focuses on an eyeground with a refraction value of 0 D. However, according to more detailed analysis, compared with measurement employing an illuminating optical system with a variable optical path length for making illumination light focus on an eyeground at any time, it is known that there is a slight deviation in the refraction value that is obtained in the case of fixing the optical path length as described above.

Figure 4:
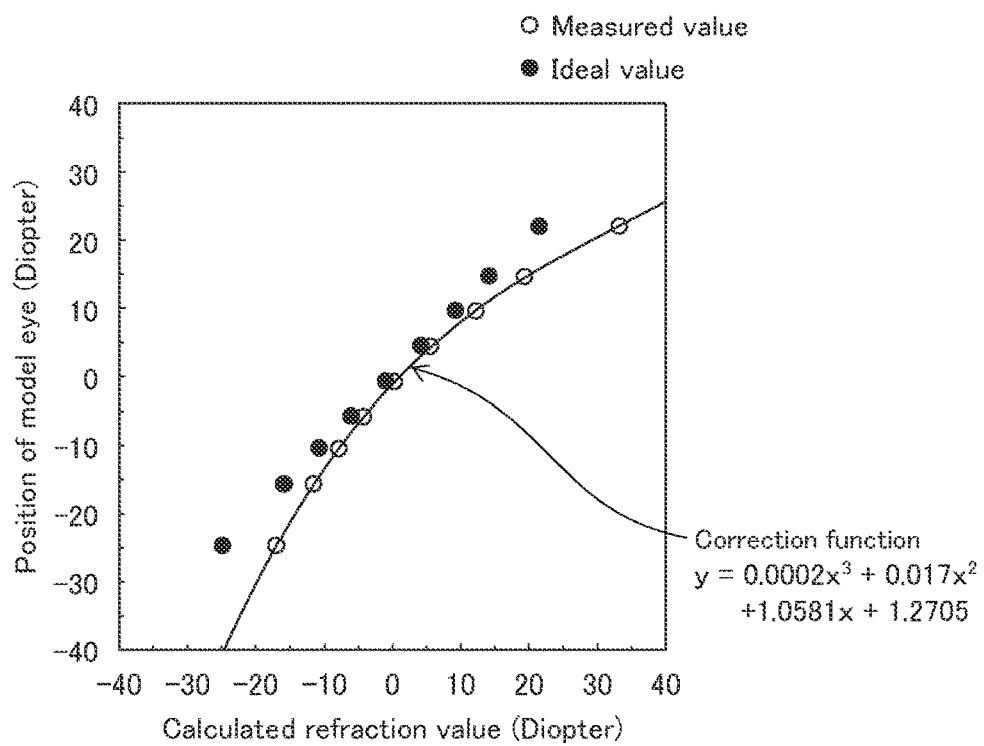
FIG. 4 is a graph showing a relationship between a calculated value (lateral axis) of a refraction value on the basis of an obtained Hartman image and a position (vertical axis) of a model eye, which is represented by a refraction value.

FIG. 4 is a graph showing a calculated value of a refraction value on the basis of an obtained Hartman image on the lateral axis and showing a position of a model eye, which is represented by a refraction value, on the vertical axis. Ideally, the measured refraction value, which is calculated on the basis of the Hartman image, and the position of the model eye have a direct proportional relationship, and plot points represented by marks "●" are obtained. For example, in measurement while the optical path length of the illuminating optical system is finely adjusted, measured values that approximately agree with the plot points represented by the marks "●" are obtained.

On the other hand, in the case of the measurement in the condition in which "the deviated amount from 0 D is −2.70 mm", the obtained refraction values based on the Hartman images form a curve that is approximately fitted by a cubic function, that is, a cubic curve, represented by marks "○" in FIG. 4. This may be caused by optical distortion that occurs due to the fixed optical path length of the illuminating optical system.

Still, as shown by the marks "○" in FIG. 4, the measured refraction values obtained in the above-described condition correctly fit to a correction function and thereby can be corrected by software processing.

Wavefront Measuring System

The ophthalmic measurement device 100 includes a Hartman plate and a wavefront measuring system. The Hartman plate splits flux of reflected light that is reflected back from an eyeground of a subject's eye into multiple light fluxes. The wavefront measuring system has a light receiving unit that receives light fluxes that are obtained as a result of splitting by the Hartman plate. The following describes the wavefront measuring system. The illumination light is emitted from the illuminating optical system 200 and is reflected back from the eyeground 151 of the subject's eye 150. This illumination light is referred to as "reflected light from the eyeground" hereinafter. The reflected light from the eyeground is reflected to the lower direction in the drawing by the dichroic mirror 109 and passes through the objective lens 108, and this light is further reflected to the right in the drawing to the lens system 106 by the dichroic mirror 107.

The reflected light from the eyeground, which has passed the lens system 106 from the left to the right direction in the drawing, is separated by the polarizing beam splitter 104. A polarized light component being a part of the separated light is mainly a polarized light component with a plane of polarization that is rotated at the eyeground, and this polarized component is reflected to the direction of the lens system 102. The flux of the reflected light from the eyeground, which is reflected from the polarizing beam splitter 104 to the lens system 102, is split into multiple light fluxes by the Hartman plate 121, and the light fluxes are received by the light receiving unit 122. The Hartman plate 121 is conjugate with the pupil of the subject's eye 150. The light receiving unit 122 is constituted of a CMOS image sensor. The light receiving unit 122 optically detects the Hartman image. The Hartman image contains wavefront information of the reflected light from the subject's eye 150, and therefore, information relating to refraction characteristics of the subject's eye, for example, a refraction value, is obtained by analyzing the Hartman image using software processing. The measured refraction characteristics of the subject's eye can be used for examination of inside of an eyeball and refractive surgery. The objective lens 108 is also used in an anterior ocular part observing system.

It is confirmed that moving the position of the light receiving unit 122 in a front-back direction to change the optical path length of the wavefront measuring system scarcely affects the measured Hartman image and has no significant effect, unlike the case of changing the optical path length of the illuminating optical system. That is, it is confirmed that moving the position of the light receiving unit 122 in the front-back direction on the optical axis scarcely changes the obtained Hartman image. This may be caused by a large NA of each lens constituting the Hartman plate 121, which provides a very large depth of focus. Thus, the position in the front-back direction of the light receiving unit 122 scarcely affects the Hartman image.

Anterior Ocular Part Illuminating System

The ophthalmic measurement device 100 includes an anterior ocular part illuminating system for illuminating an anterior ocular part of the subject's eye 151. The following describes the anterior ocular part illuminating system. The ophthalmic measurement device 100 includes a light source 112 that constitutes the anterior ocular part illuminating system. The light source 112 is an LED that generates infrared light of a wavelength of 940 nm. The light source 112 is arranged at each left and right side on a lower side of the dichroic mirror 109, although not clearly illustrated in FIG. 1. The light source 112 emits illumination light to the dichroic mirror 109, and the light, which is infrared light, is reflected at the dichroic mirror 109 and is emitted to the subject's eye 150.

Anterior Ocular Part Observing System

The ophthalmic measurement device 100 includes an anterior ocular part observing system having a light receiving unit. The light receiving unit receives light that is emitted from the anterior ocular part illuminating system and that is then reflected back from the anterior ocular part of the subject's eye 150. The following describes the anterior ocular part observing system. The illumination light is emitted from the light source 112 to the subject's eye 150 via the dichroic mirror 109. Light of a wavelength around 940 nm that is contained in this illumination light is reflected at an anterior ocular part of the subject's eye 151. This reflected light is referred to as "reflected light from the anterior ocular part" hereinafter. The reflected light from the anterior ocular part is reflected to the lower direction in FIG.

1 by the dichroic mirror 109. The reflected light from the anterior ocular part containing the light with the wavelength of 940 nm passes through the objective lens 108, is further transmitted through the dichroic mirror 107, and enters the lens system 113. The reflected light from the anterior ocular part then passes through the lens system 113 and is received by the light receiving unit 114. The light receiving unit 114 is a CCD sensor and outputs image data based on the reflected light from the anterior ocular part with the wavelength of 940 nm, that is, image data of a photographed image of the anterior ocular part. The reflected light in a visible band from the subject's eye 150 passes through the dichroic mirror 109 in the right direction in the drawing and goes outside of the ophthalmic measurement device 100.

Data Output System

The image-measuring device 100 includes an image-data outputting unit 115. The image-data outputting unit 115 outputs image data of an image of the anterior ocular part, which is obtained from the anterior ocular part observing system, to the outside. The image-data outputting unit 115 generates visualized data of refraction characteristics of the subject's eye relative to the image of the anterior ocular part on the basis of the information of a wavefront aberration, which is obtained at the light receiving unit 122, and integrates and synthesizes the generated data and the image data of the anterior ocular part. The image-data outputting unit 115 outputs the synthesized image data in addition to the image data of the anterior ocular part obtained at the light receiving unit 114. For example, the wavefront information of the reflected light from an eyeground is visually embedded in the image of the anterior ocular part to generate image data in which the wavefront information is represented as color information, and the generated image data is output. This provides an anterior ocular image that enables visually understanding the condition of the wavefront aberration or the condition of the refraction characteristics from partial differences in color.

The calculation of the refraction characteristics based on this wavefront information is performed by the computing unit 116. Of course, the computing unit 116 can calculate a refraction value in terms of a numerical value and can output this result. The computing unit 116 also performs image processing of the Hartman image by means of image processing using the calibration curve exemplified in FIG. 4 and corrects deviation in the refraction characteristics, which is described in relation to the example shown in FIG. 4. That is, a position of a bright spot constituting the Hartman image is corrected on the basis of the correction curve as shown in FIG. 4. This correction is performed by shifting the bright spot in the Hartman image by a shift amount preliminarily examined.

The calculation of the refraction characteristics is performed by the computing unit 116 and is outlined below. First, a Hartman image that is constituted of multiple light fluxes, such as 4×4 or 5×5, is used to calculate a tilt between each of the multiple light fluxes. Thereafter, information relating to the condition of light refraction in an eyeball is obtained from the angle of the tilt of each of the light fluxes.

Advantages

The positions of the light sources 201 and 202 are determined so as to have optical path lengths slightly shorter than the optical path length of the illuminating optical system 200 in which light focuses on an eyeground with a refraction value of 0 D. This enables measurement of refraction characteristics over a wide range without having to construct the lens system and the light sources of the illuminating optical system 200 so as to be movable. Either one of the light sources 201 and 202 is selected in order to obtain a clearer Hartman image, thereby further improving accuracy of the measured refraction characteristics. In this case, the optical path that provides a Hartman image with a higher brightness is selected from among the optical paths.

INDUSTRIAL APPLICABILITY

The present invention can be used in an ophthalmic measurement device that measures information relating to refraction of a subject's eye.

The invention claimed is:

1. An ophthalmic measurement device, comprising:
   an illuminating optical system having an illumination light source that illuminates an eyeground of a subject's eye;
   a light receiving optical system having a Hartman plate and a light receiving unit, the Hartman plate configured to split the flux of reflected light that is reflected back from the eyeground of the subject's eye into multiple light fluxes, and the light receiving unit configured to receive light fluxes that are obtained as a result of splitting by the Hartman plate; and
   a computing unit that calculates optical characteristics of the subject's eye from data of a tilt angle of the light flux obtained by the light receiving optical system;
   wherein the illumination light source is disposed at a predetermined position;
   a structure for moving light focusing positions of the illuminating optical system and the light receiving optical system is not provided;
   wherein an optical path length of the illuminating optical system is fixed, and the predetermined position of the illumination light source is set so that the optical path length is shorter than the optical path length in a case of focusing light on the eyeground in measuring the subject's eye with 0 D; and
   wherein the optical path length is set in a range that is approximately 2.5 to 3 mm shorter than the optical path length in measuring the subject's eye with 0 D.

2. The ophthalmic measurement device according to claim 1, wherein the computing unit performs image processing on an image obtained by the light receiving optical system and obtains the data of the tilt angle from the image that is subjected to the image processing.

3. The ophthalmic measurement device according to claim 1 wherein the illuminating optical system has multiple illumination light sources that are disposed so as to have different light focusing positions.

4. The ophthalmic measurement device according to claim 1, wherein the illuminating optical system has multiple optical paths with different lengths.

5. An ophthalmic measurement device comprising:
   an illuminating optical system having an illumination light source that illuminates an eyeground of a subject's eye;
   a light receiving optical system having a Hartman plate and a light receiving unit, the Hartman plate configured to split a flux of reflected light that is reflected back from the eyeground of the subject's eye into multiple light fluxes, and the light receiving unit configured to receive light fluxes that are obtained as a result of splitting by the Hartman plate;
   a computing unit that calculates optical characteristics of the subject's eye from data of a tilt angle of the light flux obtained by the light receiving optical system;

wherein the illumination light source is disposed at a predetermined position so that a predetermined range of measurable refraction value is secured without having to move light focusing positions of the illuminating optical system and the light receiving optical system;

wherein an optical path length of the illuminating optical system is fixed, and the predetermined position of the illumination light source is set so that the optical path length is shorter than the optical path length in a case of focusing light on the eyeground in measuring the subject's eye with 0 D; and wherein the optical path length is set in a range that is approximately 2.5 to 3 mm shorter than the optical path length in measuring the subject's eye with 0 D.

6. The ophthalmic measurement device according to claim 5, wherein the computing unit performs image processing on an image obtained by the light receiving optical system and obtains the data of the tilt angle from the image that is subjected to the image processing.

7. The ophthalmic measurement device according to claim 5, wherein the illuminating optical system has multiple illumination light sources that are disposed so as to have different light focusing positions.

8. The ophthalmic measurement device according to claim 5, wherein the illuminating optical system has multiple optical paths with different lengths.

9. An ophthalmic measurement device comprising:
an illuminating optical system having an illumination light source that illuminates an eyeground of a subject's eye;
a light receiving optical system having a Hartman plate and a light receiving unit, the Hartman plate configured to split a flux of reflected light that is reflected back from the eyeground of the subject's eye into multiple light fluxes, and the light receiving unit configured to receive light fluxes that are obtained as a result of splitting by the Hartman plate; and
a computing unit that calculates optical characteristics of the subject's eye from data of a tilt angle of the light flux obtained by the light receiving optical system;
wherein an optical path length of the illuminating optical system is fixed, and a relationship between a refraction value on a basis of a Hartman image and a refraction value of a model eye in the condition that the optical path is fixed, is preliminarily obtained, and
the computing unit performs image processing on an image obtained by the light receiving optical system, on a basis of the preliminarily obtained relationship, and obtains the data of the tilt angle from the image that is subjected to the image processing.

10. The ophthalmic measurement device according to claim 9, wherein the optical path length is set in a range that is approximately 2.5 to 3 mm shorter than the optical path length in measuring the subject's eye with 0 D.

* * * * *